United States Patent [19]
Haber et al.

[11] Patent Number: 5,135,507
[45] Date of Patent: Aug. 4, 1992

[54] ONE-PIECE SYRINGE

[75] Inventors: Terry M. Haber, Lake Forest; Clark B. Foster, Laguna Niguel; William H. Smedley, Lake Elsinore, all of Calif.

[73] Assignee: Habley Medical Technology Corporation, Laguna Hills, Calif.

[21] Appl. No.: 521,704

[22] Filed: May 10, 1990

[51] Int. Cl.$^5$ .............................................. A61M 5/00
[52] U.S. Cl. ................................... 604/187; 604/110; 604/218; 604/223
[58] Field of Search .............. 604/110, 187, 218, 220, 604/223, 233, 181, 184; 128/919

[56] References Cited

U.S. PATENT DOCUMENTS

| | | | |
|---|---|---|---|
| 530,187 | 12/1894 | Laskey | 604/223 |
| 3,598,120 | 8/1971 | Mass | 604/220 X |
| 3,951,146 | 4/1976 | Chiquiar-Arias | 604/110 |
| 4,011,868 | 3/1977 | Friend | 604/218 X |
| 4,944,730 | 7/1990 | Plucinski | 604/187 |
| 4,968,303 | 11/1990 | Clarke | 604/187 |

FOREIGN PATENT DOCUMENTS

| | | | |
|---|---|---|---|
| 0546372 | 3/1932 | Fed. Rep. of Germany | 604/187 |
| 0509675 | 11/1920 | France | 604/223 |
| 0331913 | 7/1936 | Italy | 604/218 |

Primary Examiner—C. Fred Rosenbaum
Assistant Examiner—Mark O. Polutta
Attorney, Agent, or Firm—Townsend and Townsend

[57] ABSTRACT

A one-piece syringe (2) includes an elongate frame (4) having front and back parts (6, 8) coupled by a hinge (10). A hollow barrel (12) extends from the front part and away from an outer surface (22). A plunger (14) having gaskets (54, 56) at its outer end (32) extends from the back part away from the inner surface (50). The frame is folded over at the hinge and the outer end of the plunger is inserted into the bore of the barrel. The plunger has a bendable region (62) along its length which permits the plunger to move properly along the bore during use. Withdrawal of the outer end of the plunger from the bore is prevented by the engagement of wedge shaped teeth (64) extending laterally from the plunger which engage and score the bore wall (70). After use, the barrel and plunger are pivoted to a disposal position generally parallel to the front part of the frame. This causes the frangible connection (26) between the plunger and the frame to break further preventing the reuse of the syringe. The frame is then pivoted back upon itself and latched together (92, 94) to capture the needle (36), barrel and plunger between the front and back parts for safe disposal. The frame can include slide type fasteners (128-134) to permit the syringes to be temporarily held together as a bandolier (126). A self-dispensing, lockable package (138) of syringes can be used to dispense the syringes one at a time.

39 Claims, 5 Drawing Sheets

FIG. 8

ONE-PIECE SYRINGE

BACKGROUND OF THE INVENTION

It is well recognized that syringes, if reused, present a serious problem by potentially spreading disease. In response to this, disposable syringes have been developed. One of the shortcomings with disposable syringes is their cost. This is especially true in less developed areas of the world. Although there has been much progress in this area, there still exists a need for an inexpensive, disposable syringe suitable for mass inoculations of premeasured doses of medicine.

SUMMARY OF THE INVENTION

The present invention is directed to a syringe structure or the like which can be made as a molded, substantially one-piece product (with the exception of a metal needle) specially suited for use for mass inoculations and other situations in which fixed doses are to be given.

The syringe includes an elongate frame having a front part and a back part coupled by a hinge. A hollow barrel is connected to the front part and extends generally normal to the front part in a direction away from an outer surface of the frame. The syringe also includes a plunger having one or more gaskets at its outer end which are sized to engage the bore of the barrel. The plunger is connected to the back part and extends generally normal to the back part of the frame in a direction away from the inner surface of the frame.

The front and back parts are pivoted towards one another about the hinge to permit the outer end of the plunger to be inserted into the bore of the barrel. The plunger has a bendable region along its length, preferably a necked-down region, which permits the outer end of the plunger to move properly along the bore of the barrel.

The barrel has an ejection opening at its distal end at which a hollow needle is located. The needle may be an integral part of the barrel, which is a typically plastic material, or it can be a separately made, typically metal, needle, mounted to the barrel in a conventional manner.

Withdrawal of the outer end of the plunger from the barrel is prevented by the engagement of wedge-shaped teeth extending laterally from the plunger. The teeth engage and score the wall of the bore as the plunger moves forward along the bore. The teeth are configured to restrict or prevent removal of the outer end of the plunger from the barrel by digging into the bore wall upon attempted removal. To enhance this ability, the bore wall has external recesses opposite the teeth so that the portions of the bore wall opposite the teeth are thinner than the remainder of the bore wall to enhance the deformation action of the teeth.

The barrel is pivotally mounted to the front part of the frame so that after injection the barrel, with the plunger therein, can be pivoted from the use position, generally perpendicular to the front part of the frame, to a disposal position, generally parallel to the front part of the frame. Doing so causes the frangible connection between the plunger and the back part of the frame to break further destroying the ability to reuse syringe. The frame is then pivoted completely back around the hinge part until the outer surface portions of the front and back part of the frame are opposed. Doing so captures the needle, barrel and plunger therewith between the front and back parts of the frame. The front and back frame parts are clipped or latched together in this discard orientation for safe disposal.

The front and back parts of the frame preferably include complementary projections which deform the needle when the outer surface portions of the front and back frame parts are positioned opposite one another and locked together in the discard orientation. This further ensures the syringe will not be reused.

Typically the syringe will be of plastic with a separate metal needle or cannula. The needle may be mounted to the barrel at the ejection opening in a variety of ways. One way would be to secure the needle to the distal end of the barrel after the barrel, together with the frame and plunger, have been molded.

A removable sheath may be used with the syringe. The sheath can be a separately molded part or it can be molded together with the frame through a frangible connection with frame. Another alternative would be to have the needle partially enclosed within and carried by the sheath. The needle and sheath could then be removed from the frame and secured to the distal end of the barrel by the user at the time of use.

Another feature of the invention is the provision of a bore having a larger diameter entrance bore and smaller diameter main bore, together with gaskets at the outer end of the plunger of different diameters. The outermost gasket can be sized to properly engage the main bore while the innermost gasket is sized to engage the larger diameter entrance bore. The axial dimension of the entrance bore is sufficient so that both the main bore gasket and the entrance bore gasket can fit within the entrance bore. In this way the syringe can be filled with the injectant and sealed by the entrance bore gasket engaging the bore wall at the entrance bore. However, the main bore gasket, being positioned within the entrance bore during storage, is not deflected. Therefore, when it is time to use the syringe, the main bore gasket will not have suffered compression set during storage to ensure a tight seal between the main bore gasket and the bore wall of the main bore during use. Note that any compression set suffered by the main bore gasket during storage is not critical because the injectant is not under the level of pressure it is under when the injectant is forced through the hollow needle during use.

A further aspect of the invention is the provision of catches or fasteners on the frame which allow individual syringes to be secured to one another to form a bandolier of syringes but easily separated when desired. The bandolier of syringes can be shipped and stored in a relatively rigid, preferably self-dispensing and locking, package. Individual syringes can be removed from the package and easily separated from the remaining syringes, which remain in the package.

Information regarding the contents of the syringe, in alphanumeric or coded form, such as bar coded form, may be placed on the syringe, preferably at the time of filling. Also, if known, patient information may also be marked on the syringe as well.

Other features and advantages of the invention will appear from the following description in which the preferred embodiments have been set forth in detail in conjunction with the accompanying drawings.

DETAILED DESCRIPTION OF THE PREFERRED EMBODIMENT

Figures 1, 2, 3:
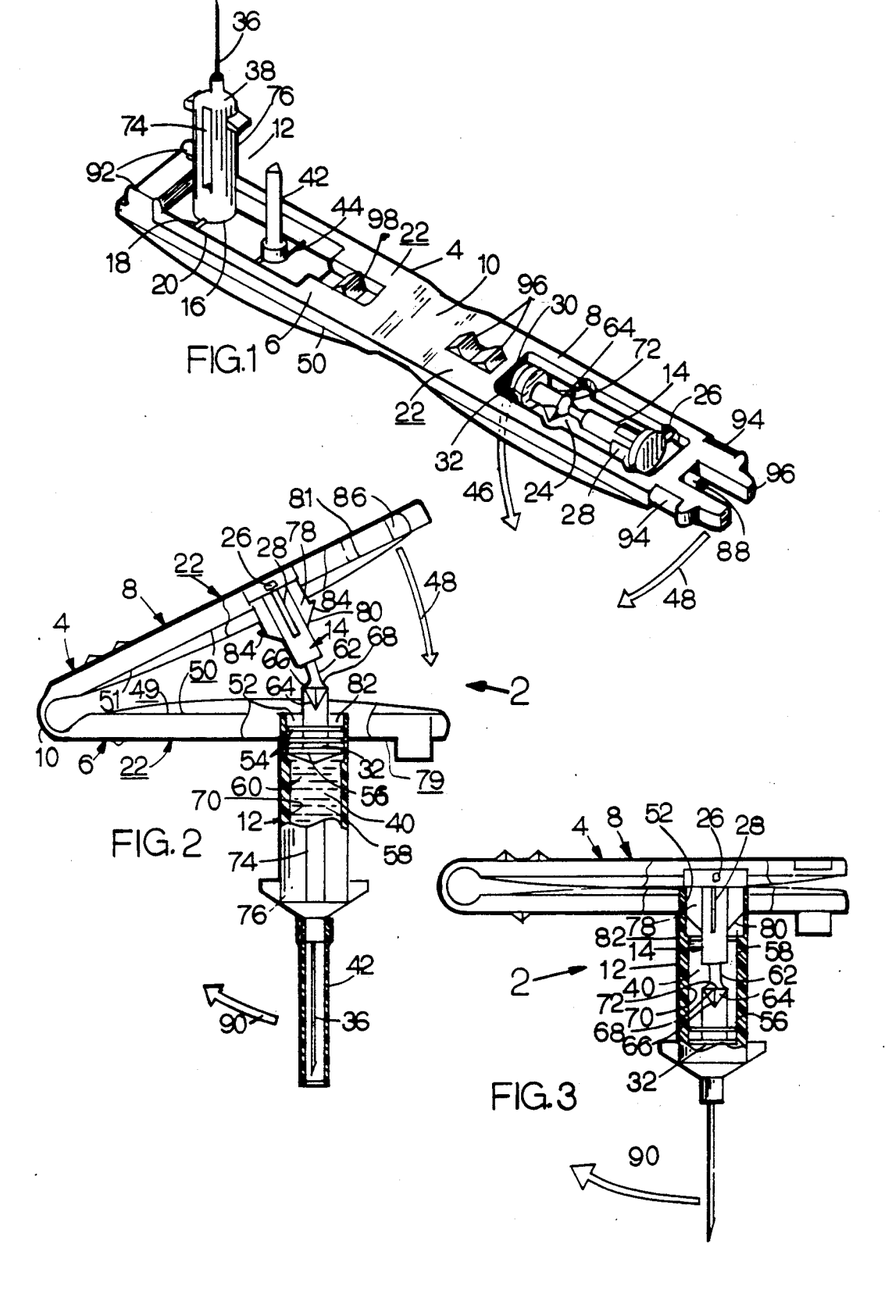
FIG. 1 is an isometric view of a syringe made according to the invention in its as-molded configuration with a needle mounted to the distal end of the barrel.
FIG. 2 shows the syringe of FIG. 1 with the plunger moved from the as-molded configuration of FIG. 1 to a use position with its outer end engaged within the entrance bore portion of the bore.
FIG. 3 illustrates the syringe of FIG. 2 with the outer end of the plunger fully engaged within the bore of the barrel at the end of the injection.

FIG. 1 illustrates a syringe 2 made according to the invention in its as-molded configuration. Syringe 2 is seen to include an elongate frame 4 having a front part 6, a back part 8 and a connecting hinge part 10. Frame 4 is a molded plastic part made of a suitable plastic material such as Himont Brand PF 511 polypropylene. Syringe 2 also includes a barrel 12 and a plunger 14. Barrel 12 and plunger 14 are integrally molded with frame 4. Proximal end 16 of barrel 12 is connected to front part 6 within a cutout 20 formed in the front part by a pair of stiff but twistable connections 18. Barrel 12, as shown in FIG. 1, extends generally normal to part 6 in a direction away from the outer surface 22 of frame 4.

Plunger 14 is molded to lie within a cutout 24 formed in back part 8 of frame 4. Plunger 14 is connected to back part 8 by pivot connections 26 at the inner end 28 of the plunger and at a frangible connection 30 at the outer end 32 of plunger 14.

A hollow needle or cannula 36 is mounted to the distal end 38 of barrel 12. Needle 36 is, in the embodiment of FIGS. 1-6, a conventional cannula used for medical injections and communicates with bore 40 formed within barrel 12. See FIGS. 2 and 6. Syringe 2 also includes a removable sheath 42 integrally formed with frame 4 and connected to front part 6 through frangible connections 44. Removable sheath 42 is normally mounted to distal end 38 of barrel 12 to cover cannula 36 for both sanitary and protective reasons. This can be accomplished manually or automatically.

To transform syringe 2 from the as-molded configuration of FIG. 1 to the use orientation of FIG. 2, outer end 32 of plunger 14 is pivoted downwardly in the direction of arrow 46 breaking frangible connection 30 while pivoting around pivot connections 26. Back part 8 is pivoted about hinge part 10 in the direction of arrow 48 so that the portion 49 of inner surface 50 of front part 6 of frame 4 generally faces the portion 51 of inner surface 50 of back part 8 of frame 4 as suggested in FIG. 2. This is accompanied by placing outer end 32 of plunger 14 into the entrance bore portion 52 of bore 40 as shown in FIG. 2.

Plunger 14 has a pair main bore gaskets 54 and an entrance bore gasket 56 at its outer end 32. Entrance bore gasket 56 is sized to matingly engage entrance bore portion 52 while main bore gaskets 54 are sized to matingly engage the main bore portion 58 of bore 40. Main bore portion 58 has a smaller diameter than entrance bore portion 52. Doing so permits syringe 2 to be shipped filled with an injectant 60 while keeping main bore gaskets from compression set during storage. Compression set for entrance bore gasket 56 is not critical there is very little if any pressure being exerted by plunger 14 on the injectant 60 during storage and transit. This ensures a tight seal between main bore gaskets 54 and main bore portion 58 during use, during which much higher pressures are created within bore 40 and which must be resisted gaskets 54, 56.

To accommodate the misalignment of pivot connections 26 and bore 40 as back part 8 moves from the beginning use orientation of FIG. 2 to ending use orientation of FIG. 3, plunger 14 includes a flexible or bendable region 62. In this preferred embodiment bendable region 62 is simply a necked down portion of plunger 14 which permits plunger 14 to bend or flex about region 62 during use.

Syringe 2 is primarily intended to be a one use, disposable syringe. To help insure that syringe 2 is only used once, plunger 14 has a pair of radially extending wedge shaped teeth 64 positioned between outer end 32 and region 62. Teeth 64 each include a leading inwardly and forwardly tapering leading edge 66 terminating at a tip 68 which is positioned to scoringly engage bore wall 70 of main bore portion 58. The teeth each have a trailing surface 72 which generally perpendicular to the axis of main bore portion 58. Surface 72 may also be inclined inwardly and forwardly. In either case teeth 64 basically dig into bore wall 70 as outer end 32 of plunger 14 moves through the main bore portion 58. If one were to attempt to withdraw plunger 14 from main bore portion 58 once teeth 64 have engaged bore wall 70, tips 68 of teeth 64 would dig into bore wall 70 substantially preventing this from occurring. Connections 26 may be made sufficiently weak so that such movement would cause connections 26 to break before plunger 14 had been removed from barrel 12. Also, the engagement of teeth 64 with bore wall 70 would essentially destroy the bore wall making subsequent use quite unlikely.

To enhance the effectiveness of teeth 64, barrel 12 have a pair of recesses 74 formed in the outer surface 76 of barrel 12 opposite the paths of movement of teeth 64.

This weakens the portions of bore wall 70 engaged by teeth 64 to enhance the effectiveness of teeth 64.

Plunger 14 also includes a number of ribs 78 with leading cam surfaces 80. Ribs 78 strengthen plunger 14 while cam surfaces 80 help to guide inner end 28 of plunger 14 into the bore opening 82 of bore 40. If desired, toothlike projections 84 can be used along the edges of ribs 78 to engage the bore wall 70 at the entrance bore portion 52 to further aid in the prevention of a withdrawal of plunger 14 from barrel 12.

During injection the user places his or her fingers on a portion 79 of outer surface 22 of front part 6 on either side of barrel 12. The user's thumb is placed on a portion 81 of the inner surface 50 at an end 86 of back part 8. Sheath 42 is then removed from needle 36. Sheath 42 may be placed on a sheath mounting peg 88, see FIG. 1, if desired. An injection is made by forcing back part 8 towards front part 6 in the direction of arrow 48 until syringe 2 reaches the ending use orientation of FIG. 3.

Figures 4, 5:
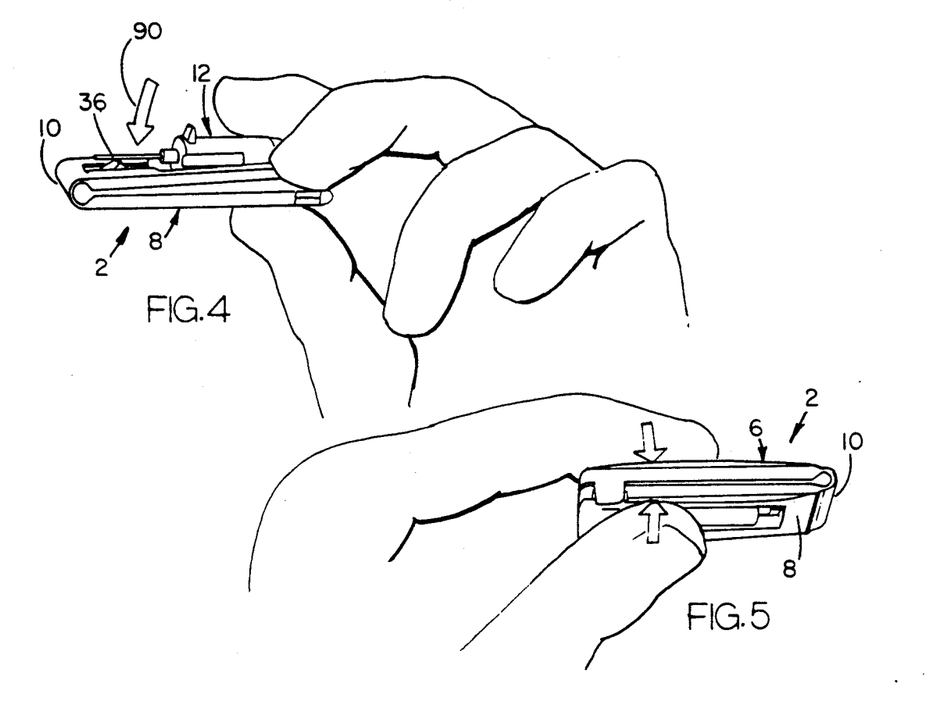
FIG. 4 illustrates a user having forced the barrel of the syringe of FIG. 3 to lie parallel to the front part of the frame after the injection.
FIG. 5 illustrates placing the syringe of FIG. 4 into the discard orientation with the barrel and needle captured between the front and back frame parts.

Since syringe 2 is intended to be a one-use, disposable syringe, it is designed to be easily and safely disposed of. To do so, as shown in FIG. 4, the user grasps the used syringe 2 and pivots barrel 12 in the direction of arrow 90 until barrel 12 and needle 36 lie generally parallel to front part 6. Doing so causes inner end 28 of plunger 14 to be separated from back part 8 through the breaking of pivot connections 26 as barrel 12 pivots about connections 18. While maintaining barrel 12, needle 36 and plunger 14 therewith in the orientation of FIG. 4, back part 8, being freed from plunger 14, is pivoted in the direction opposite arrow 48 about hinge part 10 until portions 49, 51 of inner surface 50 are opposite one another. Doing so captures barrel 12, needle 36 and plunger 14 between the front and back parts of the frame as suggested in FIG. 5. Syringe 2 is maintained in the discard orientation of FIG. 5 by the engagement of a pair of clips 92 extending from front part 6, see FIGS. 1 and 5, with complementary recesses 94 formed at end 86 of back part 8. The resulting discard orientation of FIG. 5 finds syringe 2 with its usefulness effectively destroyed and needle 36 covered to prevent accidental sticks.

Figure 6:
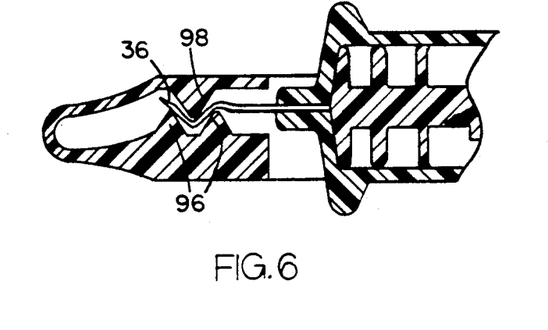
FIG. 6 is a partial cross-sectional view of the used and disabled syringe of FIG. 5 showing how the needle is bent to an unusable condition.

Frame 4 also includes a pair of extended projections 96 on back part 8 and a recessed projection 98 on front part 6. Projections 96, 98, as shown in FIGS. 1 and 6, are positioned to matingly engage one another and capture needle 36 between them to bend and thus destroy the needle captured therebetween.

Figure 7:
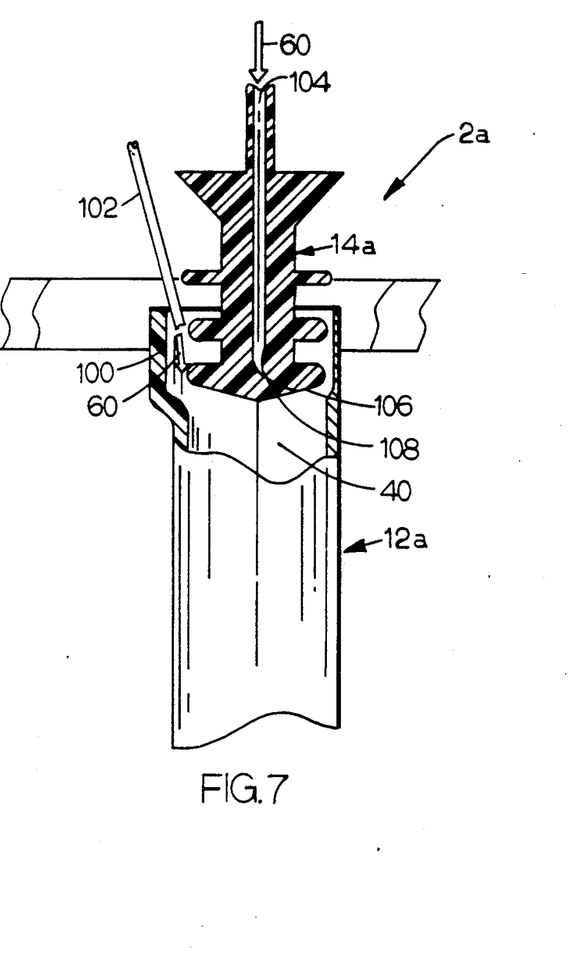
FIG. 7 illustrates two alternative methods of filling the bore of the barrel.

Several methods for filling bore 40 of barrel 12 can be used. FIG. 7 shows two methods by which this can be accomplished. In one method barrel 12a has an offset region 100 to accommodate a filler tube 102 through which injectant 60 is directed into bore 40. With a second method, plunger has an axial bore 104 through which an injectant 60 is directed. The front face 106 of plunger 14a includes a duckbill valve 108 which serves as a check valve to allow injectant 60 to pass into bore 40 from bore 104, but not the reverse. Other methods for filling bore 40, such as through needle 38, could be used as well.

Figure 8:
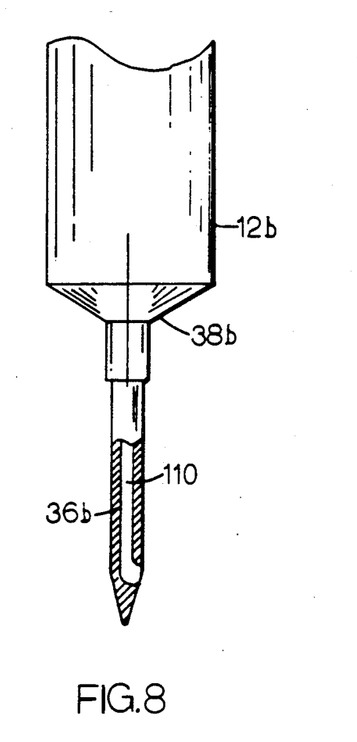
FIG. 8 illustrates the distal end of a barrel made to include a unitary molded plastic hollow needle of the type used to inject an injectant into an IV system through a rubber membrane.

Syringe 2 uses a conventional steel needle 36. However, in those cases in which syringe 2 is not intended to inject injectant 60 into tissue, needle 2 could an integral part of the barrel. As shown in FIG. 8, a needle 36b is shown at the distal end 38b of barrel 12b. Needle 36b is integrally molded with barrel 12b with a passageway 110 along its axis. This embodiment of the invention may be used for introducing an injectant 60 through a membrane and into an IV system.

Figures 9, 10, 11, 12, 13:
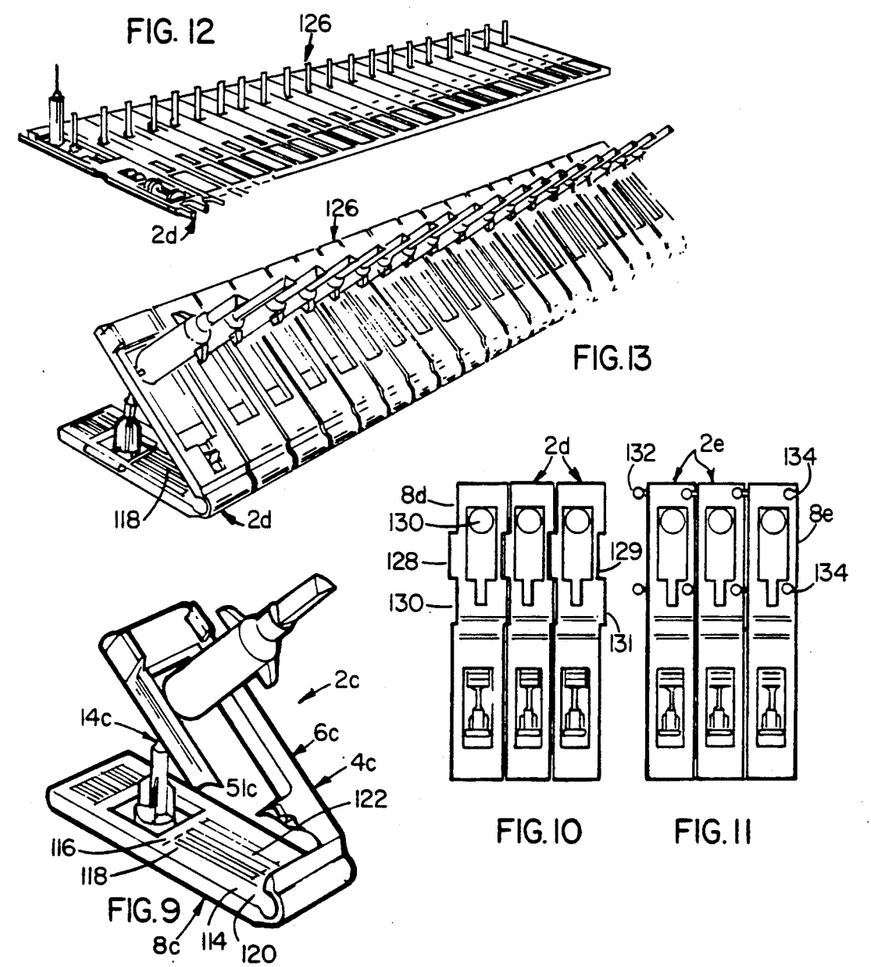
FIG. 9 is a perspective view of an alternative embodiment of the syringe of FIG. 1 with identifying information marked on a label affixed to the frame.
FIGS. 10 and 11 are simplified plan views of further alternative embodiments of the syringe of FIG. 1 illustrating two types of fasteners used to secure the frames to one another.
FIG. 12 shows a bandolier of the syringes of FIG. 10 after having been secured to one another but in the as-molded extended configurations.
FIG. 13 illustrates the bandolier of the syringes of FIG. 12, with the labels of FIG. 9, shown in the beginning use orientation.

FIG. 9 illustrates a syringe 2c at a beginning use orientation. Syringe 2c is similar to syringe 2 but has an adhesive label 114 placed on inner surface portion 51c of back part 8c of frame 4c. Label 114 has a message area 116 with identifying indicia 118 to provide the user with information. Typically the information includes information regarding the content of syringe 2c, preferably in a visually perceptible bar code 120. Syringe 2c also has patient information 122 at message area 116. The label 114 with identifying indicia 118 is preferably mounted to surface portion 51c at the time of filling syringe 2c. Indicia 116 may be printed directly on frame 4c as well. Although indicia 118 is preferably visually perceptible, indicia 118 may include non-visually perceptible information, such as information recorded on a magnetic strip.

FIGS. 10 and 11 illustrate syringes 2d, 2e in simplified form. Syringes 2d, 2e are similar to syringe 2 but with the back parts 8d, 8e modified to include fasteners which permit a group of syringes to be secured to one another in a manner shown in FIGS. 10 and 11 to create a bandolier 126 of syringes, shown in FIGS. 12 and 13. Syringes 2d include complementary sliding hinge elements 128, 129, 130, 131 which permit several syringes 2d to be removably fastened together to form bandolier 126. Syringes 2e accomplish the same result with pegs 132, having enlarged outer ends, extending laterally from one side of the back part 8e and complementary openings 134 formed on the opposite side of back part 8e. In both embodiments of FIGS. 10 and 11, the fastener elements 128-134 ensure that the syringes 2d, 2e remain fastened together but permit the user to separate adjacent syringes by sliding one relative to the other. This is achieved without undue pulling or tugging, which could cause the plunger to be forced down the barrel prematurely.

FIG. 12 illustrates a bandolier of syringes 2d in their as-molded configuration. FIG. 13 shows the bandolier 126 of syringes 2d of FIG. 12 after being manipulated into the beginning use orientation, identified with labels 114 and filled with an injectant.

Figures 14, 15, 16:
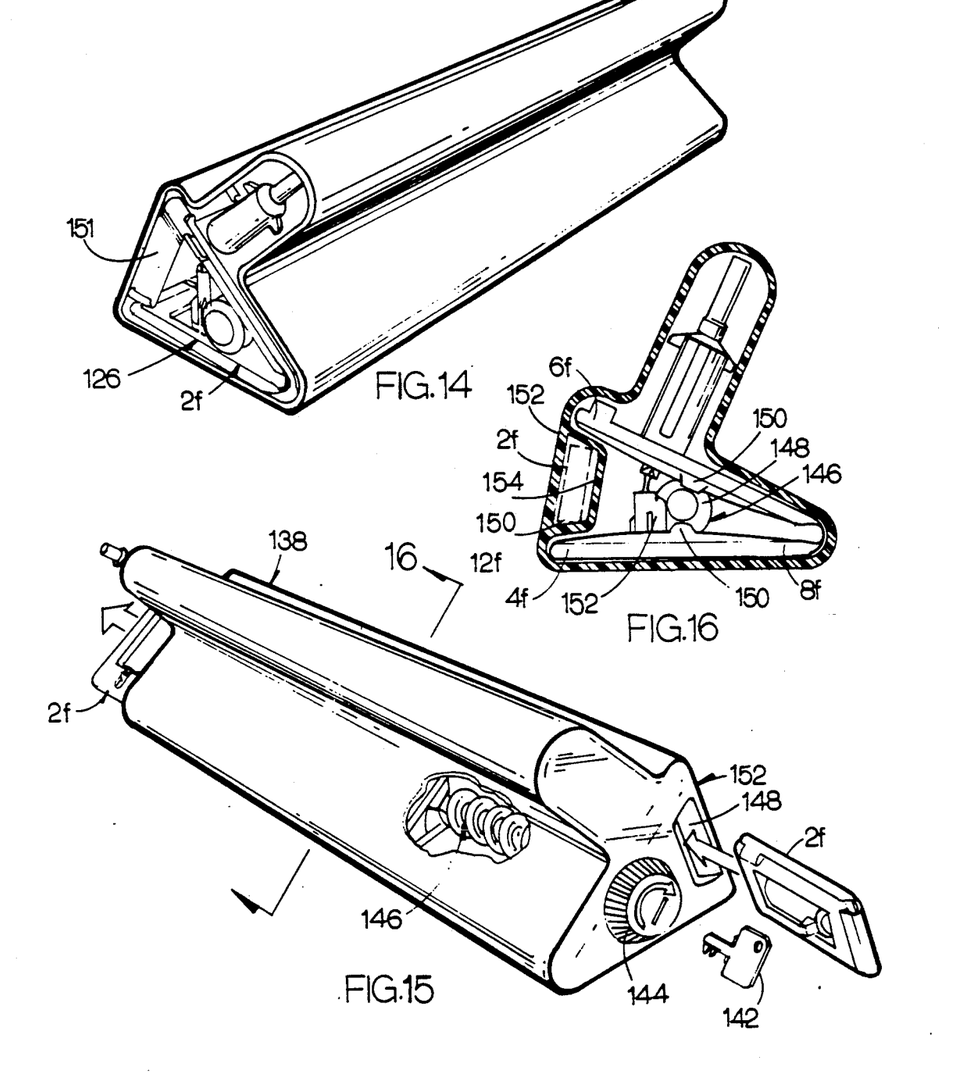
FIG. 14 shows the bandolier of syringes of FIG. 13 housed within a relatively rigid package.
FIG. 15 is a perspective view of the package of FIG. 14 showing the insertion of a used syringe through a one-way flap.
FIG. 16 is a cross-sectional view taken along line 16—16 of FIG. 15.

As illustrated in FIGS. 14-16, bandolier 126 of syringes 2f may be housed within a self-dispensing package 138 for shipping and storage. After removing an end cap (which is optional and is not shown in FIG. 14), the user removes the outermost syringe 2d from the bandolier 126 of syringes within package 138 by first inserting a key 142 into a locking knob 144. With key 142 inserted, knob 144 is rotated which drives a worm 146 extending the length of package 138. The spiral flight 148 of worm 146 engages tabs 150, 152 formed on frame 4f and barrel 2f respectively of syringes 2f. Syringes 2f are identical to syringes 2d except for the inclusion of tabs 150, 152. Thus, rotating worm 146 drives bandolier 126 of syringes 2f along package 138 until the outermost syringe 2f is free of package 138. The outermost syringe 2f is then removed from the adjacent syringe by sliding to decouple hinge elements 128, 129, 130, 131. Package 138 may then be resealed if desired. Key 142 is removed from knob 144 to prevent unauthorized dispensing of syringes 2f from package 138.

FIG. 15 illustrates a used syringe 2f in its discard orientation of FIG. 5 being inserted through a one-way flap 148 at one end of a disposal cavity 150. The other end 151 of cavity 150, shown in FIG. 14, is sealed. Cavity 150 is formed between one wall 152 of package 138 and a U-shaped extension 154 of wall 152. Cavity 150 permits at least some of syringes 2f to be housed safely after use.

Package 138 is relatively rigid to prevent inadvertent movement of the plunger down the bore of the barrel. Extension 154 also helps to ensure that front part 6f and back part 8f of frame 4f remain properly separated while stored in package 138.

Other modifications and variations may be made to the disclosed embodiments without departing from the subject of the invention as defined in the following claims. For example, package 138 could be used with syringes 2 lacking any sort of structure for connecting the syringes into a bandolier 126.

What is claimed is:

1. A syringe structure or the like comprising:
a frame having an outer surface and an inner surface, a front part, a back part and a hinge part coupling the front and back parts;
a barrel extending away from the outer surface of the front part, the barrel having a distal end, a proximal end and a bore wall defining bore between the distal and proximal ends, the barrel defining a bore opening at the proximal end and an ejection opening at the distal end;
a plunger extending away from the inner surface of the back part, the plunger including a gasket at an outer end sized for mating engagement within said bore, said plunger being bendable along its length to permit the outer end to enter into and move along the bore when the frame is folded over at the hinge part with the inner surface portions of the front and back parts being opposed; and
the frame, barrel and plunger being a one-piece, molded structure;
whereby forcing the opposed inner surface portions towards one another drives the plunger down the bore of the barrel towards the distal end to force a fluid, contained within the bore between the gasket and the ejection opening, through the ejection opening.

2. The structure of claim 1 wherein the barrel includes an integrally molded hollow needle having a passageway therealong communicating with the ejection opening.

3. The structure of claim 1 further comprising a separately manufactured hollow needle mounted to the barrel coaxial with the bore and in fluid communication with the ejection opening.

4. The structure of claim 1 wherein the plunger is pivotally attached to the back part of the frame.

5. The structure of claim 1 wherein the plunger includes external ribs at the inner end thereof.

6. The structure of claim 1 wherein the external ribs have a leading cam surface to help guide the plunger ribs into the bore opening.

7. The structure of claim 1 wherein the plunger includes a necked down central region so that the plunger can bend at the necked down central region.

8. The structure of claim 1 wherein the plunger includes a laterally extending tooth having an inwardly and forwardly tapered leading edge with a tip positioned to scoringly engage the bore wall as the plunger moves toward the distal end, the tooth having a trailing surface configured to substantially prevent effective removal of the plunger from the bore by digging into the bore wall upon attempted removal of the plunger from the bore.

9. The structure of claim 8 wherein the barrel has a reduced thickness region opposite the tooth.

10. The structure of claim 1 further comprising means for preventing effective removal of the plunger from the bore.

11. The structure of claim 10 wherein the removal preventing means include a reduced thickness region of said bore wall and wedge-shaped means for engaging the reduced thickness region.

12. The structure of claim 1 wherein the plunger includes first and second of said gaskets, the first gasket being towards the outer end and the second gasket being between the first gasket and the inner end.

13. The structure of claim 12 wherein the bore wall defines a bore having an entrance bore at the bore opening and a main bore, the entrance bore being of a larger diameter than the main bore.

14. The structure of claim 13 wherein the second gasket is sized to matingly engage the entrance bore and the first gasket is sized to matingly engage the main bore but to be undersized with respect to the entrance bore, the axial dimension of the entrance bore being sized so that both the first and second gaskets can be positioned within the entrance bore whereby compression set of the first gasket can be prevented.

15. The structure of claim 12 wherein the first gasket includes a pair of first gaskets.

16. The structure of claim 1 including means for introducing a liquid into the bore.

17. The structure of claim 16 wherein the liquid introducing means includes a plunger bore formed through the plunger and a check valve positioned along the plunger bore.

18. The structure of claim 1 wherein the barrel is pivotally attached to the front part, and wherein the plunger is frangibly attached to the back part of the frame by a frangible connection so that when the plunger is fully driven into the bore, the barrel can be pivoted relative to the frame, causing the frangible connection to break, until the barrel is generally parallel to the front part of the frame.

19. The structure of claim 18 further comprising a catch structure on the front and back parts of the frame to secure the front and back parts together into a discard orientation after the barrel has been pivoted to be generally parallel to the front part of the frame and the frame has been folded about the hinge part until the outer surface portions of the front and back parts are adjacent thereby capturing the barrel and plunger between the front and back parts.

20. The structure of claim 19 further comprising a hollow needle mounted to the barrel coaxial with and in fluid communication with the ejection opening.

21. The structure of claim 20 wherein the hollow needle and barrel are sized and positioned so the hollow needle is captured between the adjacent outer surface portions of the front and back parts when the front and back parts are in the discard orientation.

22. The structure of claim 21 further comprising means for deforming the hollow needle when the front and back parts are in the discard orientation.

23. The structure of claim 21 wherein the front and back parts include interlocking members positioned to engage and deform the hollow needle when the front and back parts are in the discard orientation.

24. The structure of claim 1 further comprising:

a hollow needle at the distal end of the barrel and in fluid communication with the ejection opening; and a sheath removably covering the hollow needle.

25. The structure of claim 24 wherein the frame includes means for securing the sheath to the frame once the sheath is removed from the hollow needle.

26. The structure of claim 24 wherein the sheath is integrally formed with the frame and attached to the frame by a frangible connection so to be removable from the frame and placed over the hollow needle.

27. The structure of claim 1 further comprising:
a sheath integrally formed with a frame and attached to the frame by a frangible connection;
a separate hollow needle at least partially enclosed within and carried by the sheath to create a needle/sheath combination;
means for mounting the needle/sheath combination to the distal end of the barrel, the sheath being separable from the needle/sheath combination when an injection is to be made.

28. The structure of claim 1 wherein the frame includes means for securing a plurality of said frames together to form a bandolier of said syringe structures.

29. The structure of claim 28 wherein said securing means includes fastener means, formed on said back parts of said frames, for slidingly securing said frames together.

30. The structure of claim 28 further comprising package means for holding said bandolier of said syringe structures and permitting one or more syringe structures to be removed from said package means and separated from any adjacent syringe structures.

31. The structure of claim 1 further comprising package means for containing a plurality of said syringe structures.

32. The structure of claim 31 wherein the package means includes means for dispensing said syringe structures from the package means one at a time.

33. The structure of claim 32 wherein the dispensing means is a locking dispensing means to help prevent unauthorized dispensing of said syringe structures from said package means.

34. The structure of claim 19 further comprising package means for containing a plurality of said syringe structures.

35. The structure of claim 34 wherein the package means includes a disposal cavity sized and configured to accept a plurality of said syringe structures in said discard orientation.

36. The structure of claim 1 wherein the frame includes indicia providing information as to the contents of the syringe structure.

37. The structure of claim 36 wherein the indicia are visual indicia.

38. The structure of claim 36 wherein the indicia include patient information.

39. The structure of claim 36 wherein the indicia include bar coded indicia.

* * * * *